United States Patent [19]

Ahlborg et al.

[11] Patent Number: 5,609,872
[45] Date of Patent: Mar. 11, 1997

[54] PEPTIDES COMPRISING A PROTECTIVE EPITOPE FROM BLOOD STAGES OF PLASMODIUM FALCIPARUM

[75] Inventors: Niklas Ahlborg, Stockholm; Klavs Berzins, Täby; Peter Perlmann, Stockholm, all of Sweden

[73] Assignee: Malvac Foundation, Stockholm, Sweden

[21] Appl. No.: 969,305

[22] PCT Filed: Aug. 16, 1991

[86] PCT No.: PCT/SE91/00541

§ 371 Date: Apr. 8, 1993

§ 102(e) Date: Apr. 8, 1993

[87] PCT Pub. No.: WO92/03159

PCT Pub. Date: Mar. 5, 1992

[30] Foreign Application Priority Data

Aug. 17, 1990 [SE] Sweden ............................... 9002684

[51] Int. Cl.$^6$ .................................................. A61K 39/015
[52] U.S. Cl. ................................. 424/185.2; 424/194.1; 424/268.1; 424/272.1; 530/300; 530/350; 530/395
[58] Field of Search .................................... 424/88, 184.1, 424/185.1, 191.1, 193.1, 268.1, 272.1, 278.1; 514/12–17, 8; 530/324–330, 395, 388.6

[56] References Cited

FOREIGN PATENT DOCUMENTS

| 0275196 | 7/1988 | European Pat. Off. | .......... C07K 7/10 |
| WO88/00597 | 1/1988 | WIPO | .............................. C07K 7/06 |

OTHER PUBLICATIONS

Ahlborg, N., et al., Mol. Biochem. Parasitol. 46:89–96 (1991), "Definition of the epitope recognized by the *Plasmodium falciparum*-reactive human monoclonal antibody 33G2".
Berzins, K., Int. J. Immunopharmacol. (in press, 1994), "Development of vaccines against malaria".
*Robbins Pathological Basis of Disease*, 4th edition, R. S. Cotran, et al. (eds.), W. B. Saunders and Company, Philadelphia (1989). Pp. 402–406 only.

Cox, F. E. G., TIBTECH 9:389–394 (Nov., 1991), "Malaria vaccines—progress and problems".
Dubois, P., et al., Ann. Inst. Pasteur/Immunol. 139:557–567 (1988), "Structure and function of a thymic peptide is mimicked by *Plasmodium falciparum* peptides".
Groux, H., et al., Eur. J. Immunol. 20:2317–2323 (1990), "Functional characterization of the antibody–mediated protection against blood stages of *Plasmodium falciparum* in the monkey *Saimiri sciureus*".
Marglin, A., et al., Ann. Rev. Biochem 39:841–866 (1970), "Chemical synthesis peptides and proteins".
Mitchell, G. H., Parasitol, 98:S29–S47 (1989), "An update on candidate malaria vaccines".
Phillips, R. E., et al., Parasitology Today 2(10):2:271–282 (1986), "The pathophysiology of severe falciparum malaria".
Udomsangpetch, R., et al., J. Immunol. 142:3620–3626 (May 15, 1989), "Reactivity of the human monoclonal antibody 33G2 with repeated sequences of three distinct *Plasmodium falciparum* antigens".
Weir, D. M., *Handbook of Experimental Immunology*, second edition (1973), pp. A2.8–A2.12.
"Structure and Function of a Thymic Peptide is Mimicked by *Plasmodium Falciparum* Peptides", Ann. Inst. Pasteur/Immunol., P. Dubois et al., vol. 139, 1988. pp. 557–567.

*Primary Examiner*—Thomas M. Cunningham
*Attorney, Agent, or Firm*—Burns, Doane, Swecker & Mathis

[57] ABSTRACT

A peptide comprising the amino acid sequence: U-O-X-glu-Z or O-X-glu-Z-ala-glu, wherein: U is an amino acid residue selected from val and ile; O is an amino acid residue selected from ala and thr: X is an amino acid residue selected from asp and glu: and Z is an amino acid residue selected from ile and val: the use of the peptide in the preparation of a vaccine; a composition for vaccination against malaria induced by *Plasmodium falciparum*, comprising such peptide in admixture with a pharmaceutically acceptable carrier; and a method of inducing immunity against malaria induced by *Plasmodium falciparum*, which comprises administering to a person in need of such immunity an effective amount of said composition.

21 Claims, 4 Drawing Sheets

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa in position 1 =Val, Ile"

( i x ) FEATURE:
        ( A ) NAME/KEY: Peptide
        ( B ) LOCATION: 2

(D) OTHER INFORMATION: /note= "Xaa in position 2 =Ala, Thr"

(ix) FEATURE:
 (A) NAME/KEY: Peptide
 (B) LOCATION: 3
 (D) OTHER INFORMATION: /note= "Xaa in position 3 =Asp, Glu"

(ix) FEATURE:
 (A) NAME/KEY: Peptide
 (B) LOCATION: 5
 (D) OTHER INFORMATION: /note= "Xaa in position 5 =Ile, Val"

(xi) SEQUENCE DESCRIPTION: SEQ ID NO:1:

```
Xaa  Xaa  Xaa  Glu  Xaa
1                    5
```

(2) INFORMATION FOR SEQ ID NO:2:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1
  (D) OTHER INFORMATION: /note= "Xaa in position 1 =Ala, Thr"

(ix) FEATURE:
  (A) NAME/KEY: Peptide
  (B) LOCATION: 2
  (D) OTHER INFORMATION: /note= "Xaa in position 2 =Asp, Glu"

(ix) FEATURE:
  (A) NAME/KEY: Peptide
  (B) LOCATION: 4
  (D) OTHER INFORMATION: /note= "Xaa in position 4 =Ile, Val"

(xi) SEQUENCE DESCRIPTION: SEQ ID NO:2:

```
Xaa  Xaa  Glu  Xaa  Ala  Glu
1                    5
```

(2) INFORMATION FOR SEQ ID NO:3:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:3:

```
Glu  Ser  Val  Thr  Glu  Glu  Ile
1                    5
```

(2) INFORMATION FOR SEQ ID NO:4:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

```
Ser  Val  Thr  Glu  Glu  Ile  Ala
1                    5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Val  Thr  Glu  Glu  Ile  Ala  Glu
1                    5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ser  Val  Thr  Glu  Glu  Ile
1                    5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Val  Thr  Glu  Glu  Ile  Ala
1                    5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Val  Thr  Glu  Glu  Ile
1                    5
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ile  Thr  Glu  Glu  Ile
1                    5
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Val  Ala  Glu  Glu  Ile
1                      5
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ile  Ala  Asp  Glu  Ile
1                      5
```

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Val  Thr  Glu  Glu  Ile
1                      5
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Thr  Glu  Glu  Ile  Ala  Glu  Glu
1                      5
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Thr  Glu  Glu  Ile  Ala  Glu
1                      5
```

(2) INFORMATION FOR SEQ ID NO:15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Glu Ser Val Thr Glu Glu Ile Ala Glu Glu Asp Lys Ser Val Ile Glu
 1               5                   10                  15
Glu Ala Val
```

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu Ser Val Thr Glu Glu Ile Ala
 1               5
```

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ile Ala Asp Glu Val
 1               5
```

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Val Glu Glu Val
 1               5
```

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Leu Val Glu Glu Val
```

1                     5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Tyr Leu Asp Glu Val
1                 5

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Glu Glu Ile Ala Glu Glu Asp
1                 5

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Glu Ile Ala Glu Glu Asp Lys
1                 5

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Ile Ala Glu Glu Asp Lys Ser
1                 5

(2) INFORMATION FOR SEQ ID NO:24:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Ala Glu Glu Asp Lys Ser Val (2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Glu Glu Asp Lys Ser Val Ile
 1               5
```

(2) INFORMATION FOR SEQ ID NO:26:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Glu Asp Lys Ser Val Ile Glu
 1               5
```

(2) INFORMATION FOR SEQ ID NO:27:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Asp Lys Ser Val Ile Glu Glu
 1               5
```

(2) INFORMATION FOR SEQ ID NO:28:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Lys Ser Val Ile Glu Glu Ala
 1               5
```

(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Ser Val Ile Glu Glu Ala Val
```

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Glu  Ser  Val  Thr  Glu  Glu
 1                    5
```

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Glu  Glu  Ile  Ala  Glu  Glu
 1                    5
```

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Glu  Ile  Ala  Glu  Glu  Asp
 1                    5
```

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Ile  Ala  Glu  Glu  Asp  Lys
 1                    5
```

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Ala  Glu  Glu  Asp  Lys  Ser
```

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Glu  Glu  Asp  Lys  Ser  Val
1                   5
```

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Glu  Asp  Lys  Ser  Val  Ile
1                   5
```

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Asp  Lys  Ser  Val  Ile  Glu
1                   5
```

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Lys  Ser  Val  Ile  Glu  Glu
1                   5
```

(2) INFORMATION FOR SEQ ID NO:39:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Ser  Val  Ile  Glu  Glu  Ala
```

(2) INFORMATION FOR SEQ ID NO:40:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Val Ile Glu Glu Ala Val
    1               5

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Glu Ser Val Thr Glu
    1             5

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Ser Val Thr Glu Glu
    1             5

(2) INFORMATION FOR SEQ ID NO:43:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Thr Glu Glu Ile Ala
    1             5

(2) INFORMATION FOR SEQ ID NO:44:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Glu Glu Ile Ala Glu ( 2 ) INFORMATION FOR SEQ ID NO:45:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

Glu Ile Ala Glu Glu
    1                5

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

Ile Ala Glu Glu Asp
    1                5

( 2 ) INFORMATION FOR SEQ ID NO:47:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

Ala Glu Glu Asp Lys
    1                5

( 2 ) INFORMATION FOR SEQ ID NO:48:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

Glu Glu Asp Lys Ser
    1                5

( 2 ) INFORMATION FOR SEQ ID NO:49:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

Glu Asp Lys Ser Val (2) INFORMATION FOR SEQ ID NO:50:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Asp Lys Ser Val Ile
1                   5

(2) INFORMATION FOR SEQ ID NO:51:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

Lys Ser Val Ile Glu
1                   5

(2) INFORMATION FOR SEQ ID NO:52:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

Ser Val Ile Glu Glu
1                   5

(2) INFORMATION FOR SEQ ID NO:53:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Val Ile Glu Glu Ala
1                   5

(2) INFORMATION FOR SEQ ID NO:54:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

Ile Glu Glu Ala Val (2) INFORMATION FOR SEQ ID NO:55:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

Glu Ser Val Thr
    1

(2) INFORMATION FOR SEQ ID NO:56:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Ser Val Thr Glu
    1

(2) INFORMATION FOR SEQ ID NO:57:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Val Thr Glu Glu
    1

(2) INFORMATION FOR SEQ ID NO:58:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Thr Glu Glu Ile
    1

(2) INFORMATION FOR SEQ ID NO:59:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Glu Glu Ile Ala (2) INFORMATION FOR SEQ ID NO:60:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

Glu Ile Ala Glu
    1

(2) INFORMATION FOR SEQ ID NO:61:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Ile Ala Glu Glu
    1

(2) INFORMATION FOR SEQ ID NO:62:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Ala Glu Glu Asp
    1

(2) INFORMATION FOR SEQ ID NO:63:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Glu Glu Asp Lys
    1

(2) INFORMATION FOR SEQ ID NO:64:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Glu Asp Lys Ser (2) INFORMATION FOR SEQ ID NO:65:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:65:

Asp Lys Ser Val
 1

(2) INFORMATION FOR SEQ ID NO:66:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:66:

Lys Ser Val Ile
 1

(2) INFORMATION FOR SEQ ID NO:67:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:67:

Ser Val Ile Glu
 1

(2) INFORMATION FOR SEQ ID NO:68:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:68:

Val Ile Glu Glu
 1

(2) INFORMATION FOR SEQ ID NO:69:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:69:

Ile Glu Glu Ala (2) INFORMATION FOR SEQ ID NO:70:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:70:

Glu Glu Ala Val
    1

PEPTIDES COMPRISING A PROTECTIVE EPITOPE FROM BLOOD STAGES OF PLASMODIUM FALCIPARUM

The present invention relates to new peptides, their use as active ingredients in vaccines and compositions containing same.

This application claims priority from PCT Application SE91/00541 and Swedish application 9002684.

BACKGROUND OF THE INVENTION

Malaria is a wide spread disease, particularly in the developing countries, and scientists are constantly looking for new means to control the dangerous parasitic disease caused by plasmodial parasites. Among these parasites *Plasmodium falciparum* causes the most severe disease, responsible for the major part of the mortality due to malaria.

One strategy in combatting malaria resides in the use of a conventional vaccine based on attenuated or dead malaria parasites, but such approach has not been found to be practically feasible.

The alternatives are constituted by development of modern techniques, such as the manufacture of proteins by chemical synthesis or by DNA technology, such proteins as components in subunit vaccines being able to induce protective immunity against the parasite infection.

One strategy in the selection of antigenic sequences to be included in a potential subunit vaccine against *Plasmodium falciparum* malaria is to define the epitopes of antibodies which have the capacity to interfere with the parasite life cycle. Properly presented in immunogens these epitopes are expected to induce protective antibody responses. With regard to the asexual blood-stages of *P. falciparum*, the main attention in this context has been made to antibodies with capacity to inhibit merozoite reinvasion in vitro (Anders, R. F. (1985) Candidate antigens for an asexual blood-stage vaccine. Parasitol. Today 1, 152–155). However, antibodies which inhibit the cytoadherence of infected erythrocytes to endothelial cells (Howard, R. J. (1988) Malarial proteins at the membrane of *Plasmodium falciparum*-infected erythrocytes and their involvement in cytoadherence to endothelial cells. Prog.Allergy 41, 98–147; Udomsangpetch, R., Aikawa, M., Berzins, K., Wahlgren, M. and Perlmann, P. (1989) Cytoadherence of knobless *Plasmodium falciparum*-infected erythrocytes and its inhibition by a human monoclonal antibody. Nature 338, 763–765) or inhibit rosette formation between uninfected and infected erythrocytes (Carlsson, J., Holmquist, G., Taylor, D. W., Perlmann, P. and Wahlgren, M. (1990) Antibodies to a histidine-rich protein (PfHRP1) disrupt spontaneously formed *Plasmodium falciparum* erythrocyte rosettes. Proc.Natl.Acad. Sci. USA 87, 2511–2515) may also be of interest. Such antibodies are expected to interfere in vivo with the sequestration of late-stage infected erythrocytes (Howard, R. J. (1988) Malarial proteins at the membrane of *Plasmodium falciparum*-infected erythrocytes and their involvement in cytoadherence to endothelial cells. Prog.Allergy 41, 98–147; Carlson, J., Holmquist, G., Taylor, D. W., Perlmann, P. and Wahlgren, M. (1990) Antibodies to a bistidine-rich protein (PfHRP1) disrupt spontaneously formed *Plasmodium falciparum* erythrocyte rosettes. Proc.Natl.Acad.Sci. USA 87, 2511–2515).

The human monoclonal antibody (mAb) 33G2, obtained from an Epstein-Barr virus transformed B-cell originating from a Liberian *P.falciparum*-immune donor (Udomsangpetch, R., Lundgren, K., Berzins, K., Wahlin, B., Perlmann, H., Troye-Blomberg, M., Carlsson, J., Wahlgren, M., Perlmann, P. and Björkman, A. (1986) Human monoclonal antibodies to Pf155, a major antigen of malaria parasite *Plasmodium falciparum*. Science 231, 57–59) has several interesting biological properties. It inhibits both *P.falciparum* merozoite reinvasion in in vitro cultures (Udomsangpetch, R., Lundgren, K., Berzins, K., Wahlin, B., Perlmann, H., Troye-Blomberg, M, Carlson, J., Wahlgren, M., Perlmann, P. and Björkman, A. (1986) Human monoclonal antibodies to Pf155, a major antigen of malaria parasite *Plasmodium falciparum*. Science 231, 57–59) as well as cytoadherence of infected erythrocytes to melanoma cells in vitro (Udomsangpetch, R., Aikawa, M., Berzins, K., Wahlgren, M. and Perlmann, P. (1989) Cytoadherence of knobless *Plasmodium falciparum*-infected erythrocytes and its inhibition by a human monoclonal antibody. Nature 338, 763–765). The mAb, thus, has the capacity to interfere with the parasite erythrocytic life cycle at two potential target sites for protective antibodies in vivo (Anders, R. F. (1985) Candidate antigens for an asexual blood-stage vaccine. Parasitol. Today 1, 152–155) which makes the epitope recognized by the mAb of great interest with regard to vaccine development.

The mAb 33G2 was initially selected due to its reactivity with Pf155/RESA as detected by erythrocyte membrane immunofluorescence (EMIF) and immunoblotting (Udomsangpetch, R., Lundgren, K., Berzins, K., Wahlin, B., Perlmann, H., Troye-Blomberg, M., Carlsson, J., Wahlgren, M., Perlmann, P. and Björkman, A. (1986) Human monoclonal antibodies to Pf155, a major antigen of malaria parasite *Plasmodium falciparum*. Science 231, 57–59) but subsequent analyses with recombinant fusion proteins and synthetic peptides revealed that the antibody showed reactivity with a family of cross-reacting *P.falciparum* blood-stage antigens, including Pf155/RESA, Pf11.1 and Ag332 (Mattei, D., Berzins, K., Wahlgren, M., Udomsangpetch, R., Perlmann, P., Griesser, H. W., Scherf, A., Müller-Hill, B., Bonnefoy, S., Guilotte, M., Langsley, G., Pereira da Silva, L. and Mercereau-Puijalon, O. (1989) Cross-reactive antigenic determinants present on different *Plasmodium falciparum* blood-stage antigens. Parasite Immunol. 11, 15–30; Mercereau-Puijalon, O., Langsley, G., Mattei, D., Guilotte, M., Blisnick, T., Berzins, K., Griesser, H. W., Scherf, A., M üller-Hill, B. and Pereira da Silva, L. (1987) Presence of cross-reacting determinants on several blood-stage antigens of *Plasmodium falciparum*. UCLA Symp.Molec. Cell.Biol. 42, 343354; Udomsangpetch, R., Carlsson, J., Wahlin, B., Holmquist, G., Ozaki, L. S., Scherf, A., Mattei, D., Mercereau-Puijalon, O., Uni, S., Aikawa, M., Perzins, K. and Perlmann, P. (1989) Reactivity of the human monoclonal antibody 33G2 with repeated sequences of three distinct *Plasmodium falciparum* antigens. J. Immunol. 142, 3620–3626). A feature shared between these antigens is their contents of several tandemly repeated amino acid sequences containing regularly spaced pairs of glutamic acid (Mattei, D., Berzins, K., Wahlgren, M., Udomsangpetch, R., Perlmann, P., Griesser, H. W., Scherf, A., Müller-Hill, B., Bonnefoy, S., Guillotte, M., Langsley, G., Pereira da Silva, L. and Mercereau-Puijalon, O. (1989) Cross-reactive antigenic determinants present on different *Plasmodium falciparum* blood-stage antigens. Parasite Immunol. 11, 15–30; Favaloro, J. M., Coppel, R. L., Corcoran, L. M., Foote, S. J., Brown, G. V., Anders, R. F. and Kemp, D. J. (1986) Structure of the RESA gene of *Plasmodium falciparum*. Nucleic Acids Res. 14, 8265–8277; Scherf, A., Hilbich, C., Sieg, K., Mattei, D., Mercereau-Puijalon, O. and M üller-Hill, B. (1988) The 11-1 gene of *Plasmodium falciparum* codes for distinct fast evolving repeats. EMBO J. 7, 1129–1137). These dimers of glutamic acid were suggested to be the structures responsible for the antigenic cross-reactions seen between the three antigens (Mattei, D., Berzins, K., Wahlgren, M., Udomsangpetch, R., Perlmann, P., Griesser, H. W., Scherf, A., Müller-Hill, B., Bonnefoy, S., Guilotte, M., Langsley, G., Pereira da Silva, L. and Mercereau-Puijalon, O. (1989) Cross-reactive antigenic determinants present on different *Plasmodium falciparum* blood-stage antigens. Parasite Immunol. 11, 15–30; Merecereau-Puijalon, O., Langsley, G., Mattei, D., Guilotte, M., Blisnick, T., Berzins, K., Griesser, H. W., Scherf, A., M üller-Hill, B. and Pereira da Silva, L. (1987) Presence of cross-reacting determinants on several blood-stage antigens of *Plasmodium falciparum*. UCLA Symp.Molec. Cell.Biol. 42, 343–354; Udomsangpetch, R., Carlsson, J., Wåhlin, B., Holmquist, G., Ozaki, L. S., Scherf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. J. Immunol. 142, 3620–3626). Inhibition with synthetic peptides of the mAb 33G2 binding in EMIF showed that peptides corresponding to Ag332 repeat sequences were the most efficient inhibitors, suggesting that Ag332 was the original target for the antibody (Udomsangpetch, R., Carlsson, J., Wåhlin, B., Holmquist, G., Ozaki, L. S., Scharf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. J. Immunol. 142, 3620–3626).

The major object of the present invention is to provide new peptides capable of inducing immunity against malaria.

Another object of the invention is to provide new compositions for vaccination against malaria comprising such peptide.

Yet another object of the invention is to provide a method of inducing immunity against malaria.

SUMMARY OF THE INVENTION

It has been found that a peptide comprising the amino acid sequence [SEQ. ID. NO. 1]:

U-O-X-glu-Z, wherein:

U is an amino acid residue selected from val and ile;
O is an amino acid residue selected from ala and thr;
X is an amino acid residue selected from asp and glu; and
Z is an amino acid residue selected from ile and val is capable of providing protective immunity against malaria induced by *Plasmodium falciparum*. Such protective immunity can be provided also by a peptide comprising the amino acid sequence [SEQ. ID. NO. 2]:

O-X-glu-Z-ala-glu, wherein

O, X and Z have the above meaning.

Preferred embodiments of the peptide of the present invention are the following:

glu-ser-val-thr-glu-glu-ile [SEQ ID NO.: 3];

ser-val-thr-glu-glu-ile-ala [SEQ ID NO.: 4];

val-thr-glu-glu-ile-ala-glu [SEQ ID NO.: 5];

ser-val-thr-glu-glu-ile [SEQ ID NO.: 6];

val-thr-glu-glu-ile-ala [SEQ ID NO.: 7];

val-thr-glu-glu-ile [SEQ ID NO.: 8];

ile-thr-glu-glu-ile [SEQ ID NO.: 9];

val-ala-glu-glu-ile [SEQ ID NO.: 10];

ile-ala-asp-glu-ile [SEQ ID NO.: 11];

Particularly preferred are the following peptides.

val-thr-glu-glu-ile [SEQ ID NOS.: 8 or 12], thr-glu-glu-ile-ala-glu-glu [SEQ ID NO.: 13], thr-glu-glu-ile-ala-glu [SEQ ID NO.: 14], Accordingly, the peptides of the present invention find medicinal use, particularly as active ingredients in vaccines, such as vaccines against malaria.

The peptides of the present invention are also useful in the preparation of vaccines, particularly vaccines for combatting malaria induced by *Plasmodium falciparum*.

The invention also covers compositions for vaccination against malaria induced by *Plasmodium falciparum*, said composition comprising a peptide selected among those defined or mentioned above in admixture with a pharmaceutically acceptable carrier. It is preferred to use carriers suitable for parenteral administration.

As is generally known within immunology the immunogenic response resulting from administration of a relatively small peptide can be enhanced in several ways.

First, it is conceivable to contain the active peptide or principal in a larger molecule, wherein said peptide is present in repeating units. Such polymerized form can be prepared using recombinant DNA techniques.

Second, the peptide can be coupled to a macromolecular carrier, such as bovine serum albumin or other immunogenic carrier or adjuvant thus inducing a better immune response against the peptide in view of the increased size of the molecule. The antigenic presentation of a small peptide in accordance with the invention can be improved for example by conjugation to a preformed iscom as a carrier (for details see Journal of Immunological Methods, 98 (1987) 137–143, K. Löfgren et al.).

The composition of the present invention can be constituted by a solution, a suspension or other form of preparation. Such solutions or suspensions may take the form of sterilized aqueous isotonic preparations, such as isotonic saline solution or glucose solution. As indicated above parenteral administration is preferred.

It goes without saying that although the peptides of the invention can be used alone, combinations of two or more of same can be contained in one and the same composition.

Finally, the present invention provides a method of inducing immunity against malaria induced by *Plasmodium falciparum*, said method comprising administering to a person in need of such immunity an effective amount of the composition as defined above. The method is particularly exercised in the form of parenteral injection.

In the present disclosure the abbreviations used have the following meanings:
A=ala=alanine;
D=asp=aspartic acid;
C=cys=cysteine
E=glu=glutamic acid;

I=ile=isoleucine;
L=leu=leucine
R=lys=lysine
F=phe=phenylalanine
P=pro=proline
S=ser=serine
T=thr=threonine; and
W=trp=tryptophan
Y=tyr=tyrosine
V=val=valine.

EXAMPLES

The present invention will be described more detailed in the following specific examples. Said examples are not to be construed to limit the scope of the invention otherwise as defined in the appended claims. The examples are given with reference to the appended drawings, wherein:

EXAMPLE 1

Figure 1A:
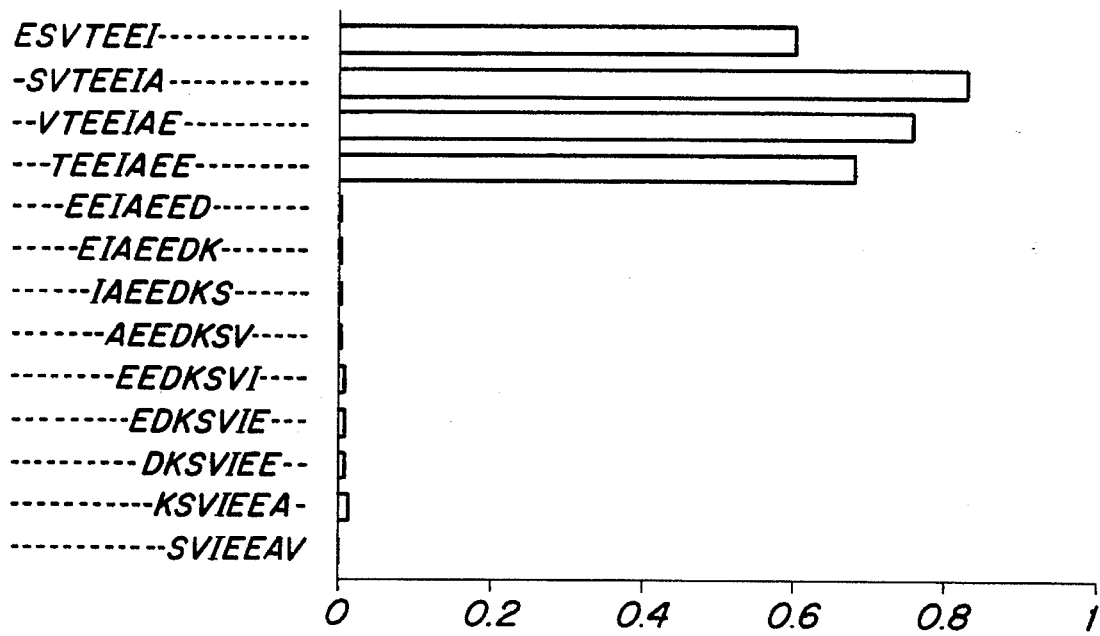
FIG. 1a shows antibody reactivity of four heptapeptides [SEQ ID NOS.: 3, 4, 5 and 13] according to the invention expressed as absorbance at 405 nm.

Establishment of a human B-cell line producing the monoclonal antibody 33G2.

Periferal blood lymnphocytes (PBL) were isolated by standard procedures from heparinized blood of a Liberian donor known to be immune to malaria (Udomsangpetch, R., Lündgren, K., Berzins, K., Wåhlin, B., Perlmann, H., Troye-Blomberg, M., Carlsson, J., Wahlgren, M., Perlmann, P. and Björkman, A. (1986) Human monoclonal antibodies to Pf155, a major antigen of malaria parasite *Plasmodium falciparum. Science* 231, 57–59). The PBL were incubated for 3 days with *P. falciparum* parasite extract in order to activate the malaria specific B-lymphocytes (Lundgren, K., Wahlgren, M., Troye-Blomberg, M., Berzins, K., Perlmann, H. and Perlmann, P. (1983) Monoclonal anti-parasite and anti-RBC antibodies produced by stable EBV-transformed B cell lines from malaria patients. *J. Immunol.* 131, 2000–2003). For transformation of B-lymphocytes Epstein Barr virus (EBV), contained in culture medium from the EBV-producing marmoset cell line B95-8, was added to the PBL and incubated for 2 hr at 37° C. After washing, the cells were suspended at $2\times10^6$/ml in tissue culture medium (RPMI 1640 supplemented with 10% fetal calf serum, 1% glutamine and 25 µg/ml gentamicin) containing 0.2 µg/ml of cyclosporin A and then incubated in 10 ml roundbottomed tubes for 5 days at 37° C. in air +5% $CO_2$. The cells were then transferred to 50 ml tissue culture flasks for continued propagation for 9 days. Cyclosporin was present in all media during the first 2 weeks of cell propagation. Two weeks after transformation, the cells were seeded in 96-well tissue culture plates with $5\times10^5$ irradiated (4500 rad) allogeneic PBL per well as feeder cells. Immunoglobulin producing cultures were detected by measuring in enzyme linked immunosorbent assay (ELISA) (Engvall & Perlmann, Immunochemistry 8, 871–874, 1971) the presence in the culture medium of the wells of immunoglobulin. Immunoglobulin containing culture supernatants were further analyzed for the presence of antibodies to the *P. falciparum* antigen Pf155/RESA by means of indirect immunofluorescence using glutaraldehyde fixed and air dried monolayers of infected erythrocytes from *P. falciparum* in vitro cultures (Perlmann et al. J. Exp. Med. 159, 1586–1704, 1984). Cultures scoring positive in the latter assay were submitted to repeated cloning by limited dilution. Monoclonality of the antibodies produced was assessed by isoelectric focusing. The antibody producing clone 33G2 thus obtained showed high growth rate and antibody production (10–13 µg IgM/ml in 72 hours) (Udomsangpetch, R., Lundgren, K., Berzins, K., Wåhlin, B., Perlmann, H., TroyeBlomberg, M., Carlsson, J., Wahlgren, J., Perlmann, P. and Börkman, A. (1986). Human monoclonal antibodies to Pf155, a major antigen of malaria parasite *Plasmodium falciparum. Science* 231, 57–59).

EXAMPLE 2

Inhibition in vitro of malaria parasite invasion into red blood cells.

The capacity of the monoclonal antibody (mAb) 33G2 to inhibit parasite development in *P. falciparum* in vitro cultures was assayed by a procedure described by Wåhlin et al. (Proc. Nat. Acad. Sci. USA 81, 7912–7916, 1984). *P. falciparum* cultures were diluted with normal O+ erythrocytes to a parasitemia of 0.5% and a hematocrit of 2%. Aliquots of the parasite suspension (100 µl) were seeded in quadruplicate in 96-well flat-bottomed microculture plates: The mAb 33G2 was added to the wells at different concentrations, either in culture supernatant or after purification on concanavalin A-Sepharose of ammonium sulfate precipitated culture supernatants (Kleine et al. Molec. Immunol. 16, 421–425, 1979). After incubation for 20 hr at 37° C. in a candle jar (Trager & Jensen, Science 193, 673–675, 1976), the erythrocytes from each well were washed in tris-buffered Hanks solution (TH) and monolayers were prepared on eight-well multitest slides as follows. Erythrocyte suspensions were applied to slides treated with bicarbonate buffer (pH 9.6). Immediately after being washed in TH, the monolayers were fixed briefly (2×10 sec) in 1% glutaraldehyde in phosphate-buffered saline (pH 7.4), washed in distilled water and then air-dried extensively under a fan. The parasites were stained with acridine orange and the number of parasitized erythrocytes was obtained by counting $4\times10^4$ erythorcytes per sample.

Both preparations of mAb 33G2 inhibited *P. falciparum* reinvasion efficiently in a concentration dependent manner, the culture supernatant contained mAb giving 50% inhibition of reinvasion at 14 µg/ml and the purified mAb giving 50% inhibition at 5.5 µg/ml (Udomsangpetch, R., Lundgren, K., Berzins, K., Wåhlin, B., Perlmann, H., Troye-Blomberg, M., Carlson, J. Wahlgren, M., Perlmann, P. and Bj örkman, A. (1986) Human monoclonal antibodies to Pf155, a major antigen of malaria parasite *Plasmodium falciparum*. *Science* 231, 57–59).

EXAMPLE 3

Inhibition of Cytoadherence of Malaria Infected Erythrocytes to Endothelial and Melanoma Cells in Vitro The capacity of mAb 33G2 to inhibit the cytoadherence of *P. falciparum* infected erythrocytes to endothelial cells was demonstrated in an assay using the melanoma cell line C32 as described by Udeinya et al. (Exp. Parasitol. 56, 207–214, 1983). Melanoma cells grown on cover slips were fixed with 1% formaldehyde in phosphate-buffered saline (pH 7.4) and then stored at 4° C. until used. A suspension (2% hematocrit) of erythrocytes from a *P. falciparum* culture, containing mainly trophozoites and schizonts at 5–10% parasitemia, were incubated with the fixed melanoma cells at room temperature on a rotating platform for 1 hour. Unbound erythrocytes were flushed away with phosphate-buffered saline. The coverslips were then fixed with 1% glutaraldehyde in phosphate-buffered saline, stained with Giemsa and examined in the light microscope. For assaying antibody mediated inhibition of cytoadherence, pellets of infected erythrocytes (40–50 µl) were suspended in 100 µl of antibody solution (15–250 µg/ml) and incubated for 30 min at 37° C. with agitation every 10 min. The erythrocytes were then diluted to a 2% hematocrit suspension and applied to the cytoadherence assay as described above. The number of bound erythrocytes per 100 melanoma cells was counted and expressed as the percentage of bound cells:

The mAb 33G2 inhibited cytoadherence in a dose dependent manner, giving about 45% inhibition at the highest antibody concentration tested (250 µg of purified mAb per ml) (Udomsangpetch, R., Aikawa, M., Berzins, K., Wahlgren, M. and Perlmann, P. (1989) cytoadherence of knobless *Plasmodium falciparum*-infected erythrocytes and its inhibition by a human monoclonal antibody. *Nature* 338, 763–765).

EXAMPLE 4

Reactivity of Monoclonal Antibody 33G2 with Cross-reactive *P. falciparum* Antigens The mAb 33G2 was initially selected due to its reactivity with the *P. falciparum* antigen Pf155/RESA as detected by immunofluorescence and immunoblotting (see Ex. 1 and ref. 1). Analysis of antibody reactivity with different recombinant *P. falciparum* blood stage antigens was performed by immunoblotting using recombinant bacterial (*E. coli*) plaques (Mattei, D., Berzins, K., Wahlgren, M., Udomsangpetch, R., Perlmann, P., Griesser, H. W., Scherf, A., Müller-Hill, B., Bonnefoy, S., Guillotte, M., Langsley, G., Pereira da Silva, L. and Mercereau-Puijalon, O. (1989) Cross-reactive antigenic determinants present on different *Plasmodium falciparum* bloodstage antigens. *Parasite Immunol.* 11, 15–30). The mAb showed binding to bacterial plaques expressing parts of the *P. falciparum* antigens Pf11.1, Ag332 and Pf155/RESA, showing the strongest reactivity with Ag332 expressing plaques (Mattei, D., Berzins, K., Wahlgren, M., Udomsangpetch, R., Perlmann, P., Griesser, H. W., Scherf, A., Müller-Hill, B., Bonnefoy, S., Guillotte, M., Langsley, G., Pereira da Silva, L. and Mercereau-Puijalon, O. (1989). Cross-reactive antigenic determinants present on different *Plasmodium falciparum* bloodstage antigens. *Parasite Immunol.* 11, 15–30). No binding was seen to bacterial plaques expressing the *P. falciparum* antigens FIRA or Ag281. The capacity of various synthetic peptides, corresponding to repeated sequences in the antigens Pf11.1, Ag332 and Pf11/RESA, to block the binding of mAb 33G2 to Pf11/RESA as detected by immunofluorescence was analysed (Udomsangpetch, R., Carlsson, J., Wåhlin, B., Holmquist, G., Ozaki, L. S., Scherf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. *J. Immunol.* 142, 3620–3626). Different concentrations of the peptides (up to 200 µg/ml) were mixed with a fixed concentration of the mAb, which then was used in the immunofluoresce assay (see Ex. 1). The peptide Y (SVTEEIAEEDK)$_2$, corresponding to a dimer of amino acids 2–12 in antigen Ag332 (Mattei, D., Berzins, K., Wahlgren, M., Udomsangpetch, R., Perlmann, P., Griesser, H. W., Scherf, A., Müller-Hill, B., Bonnefoy, S., Guillotte, M., Langsley, G., Pereira da Silva, L. and Mercereau-Puijalon, O. (1989) Cross-reactive antigenic determinants present on different *Plasmodium falciparum* bloodstage antigens, *Parasite Immunol.* 11, 15–30), was the most efficient inhibitor of mAb binding, giving complete inhibition of immunofluorescence at 0.2 µg/ml (Udomsangpetch, R., Carlsson, J., Wåhlin, B., Holmquist, G., Ozaki, L. S., Scherf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. *J. Immunol.* 142, 3620–3626). Also some peptides corresponding to sequences in Pf11.1 and PF155/RESA inhibited mAb 33G2 immunofluorescence but with considerably less efficiency, the Pf11.1 peptide (EEVVEEVVP)$_2$ and the Pf155/RESA peptide both giving complete inhibition at 100 µg/ml. The results show that mAb 33G2 recognizes a family of cross-reactive *P. falciparum* antigens including Pf11.1, Pf155/RESA and Ag332, the latter antigen being the optimal target for the mAb (Udomsangpetch, R., Carlsson, J., Wåhlin, B., Holmquist, G., Ozaki, L. S., Scherf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. *J. Immunol.* 142, 3620–3626).

EXAMPLE 5

Determination of the Epitope Specificity of the Monoclonal Antibody 33g2

The detailed epitope specificity on the single amino acid level for the mAb 33G2 was performed using the multiple peptide synthesis technique (PEPSCAN) developed by Geysen et al. (J. Immunol. Methods 102, 259–274, 1987). Peptides were synthesized on polyethylene rods on which polymers of polyacrylic acid had been formed by 1:radiation. Polyethylene rods and Pmoc L-amino acids performed as active esthers (Cambridge Research Biochemicals, UK) were used for synthesis according to instructions of the manufacturer. The N-terminals of all peptides were acetylated. As a basis for the mAb 33G2 epitope analysis, the sequence of amino acid residues 1–19 [SEQ ID NO.: 15] (ESVTEEIAEEDKSVIEEAV) of Ag332 (Mattei, D., Berzins, K., Wahlgren, M., Udomsangpetch, R., Perlmann, P., Griesser, H. W., Scherf, A., Müller-Hill, B., Bonnefoy, S., Guillotte, M., Langsley, G., Pereira da Silva, L. and Mercereau-Puijalon, O. (1989) Cross-reactive antigenic determinants present on different *Plasmodium falciparum* blood-stage antigens. *Parasite Immunol.* 11, 15–30) was used, containing sequences of the peptides with the highest reactivity with the mAb (Udomsangpetch, R., Carlsson, J., Wåhlin, B., Holmquist, G., Ozaki, L. S., Scherf, A., Mattei, D., Mercereau-Puijalon, O., Uni, S., Aikawa, M., Berzins, K. and Perlmann, P. (1989) Reactivity of the human monoclonal antibody 33G2 with repeated sequences of three distinct *Plasmodium falciparum* antigens. *J. Immunol.* 142, 3620–3626). All possible overlapping heptapeptides, hexapeptides, pentapeptides and tetrapeptides covering the mentioned sequence were synthesized and their reactivity with mAb 33G2 was analysed by ELISA as described by Geysen et al. (J. Immunol. Methods 102, 259–274, 1987). Culture supernatant containing mAb 33G2 (approx. 10 μg/ml), was diluted 1:100. Peptide containing rods were washed in phosphate-buffered saline with 0.05% Tween 20 between all steps in ELISA. Bound antibodies were detected with a rabbit antihuman IgM-alkaline phosphatase conjugate (Sigma, St. Louis, Mo.) using p-nitrophenyl phosphate, disodium salt (Sigma) as substrate.

Figure 1B:
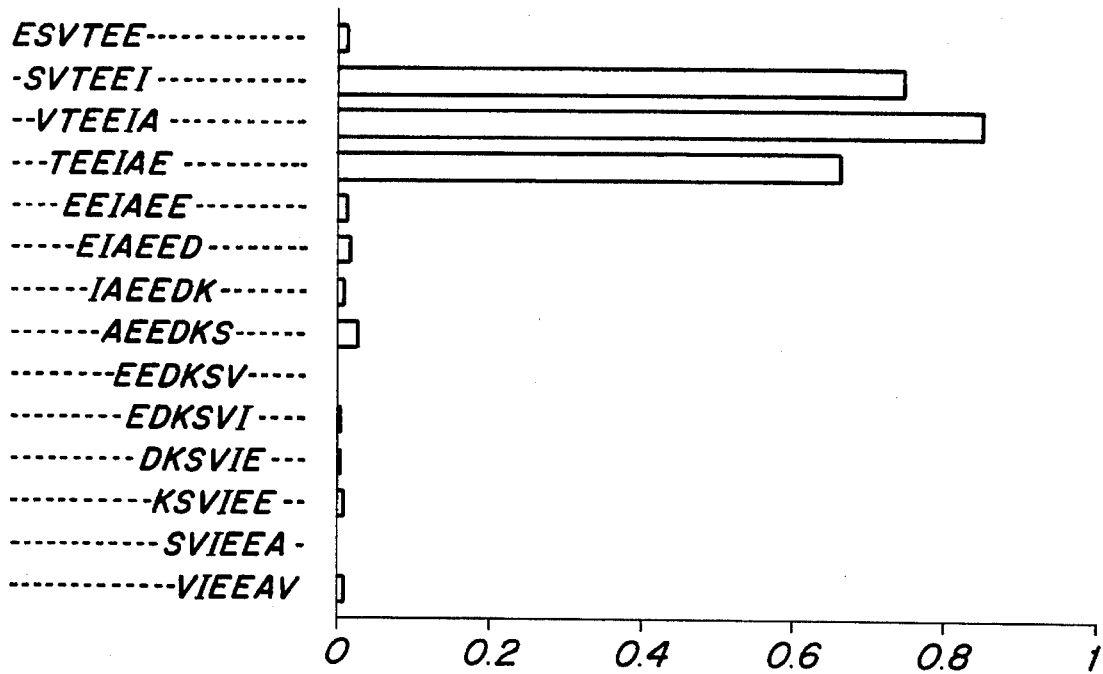
FIG. 1b shows antibody reactivity of three hexapeptides [SEQ ID NOS.: 6, 7 and 14] according to the invention expressed as absorbance at 405 nm.
Figure 1C:
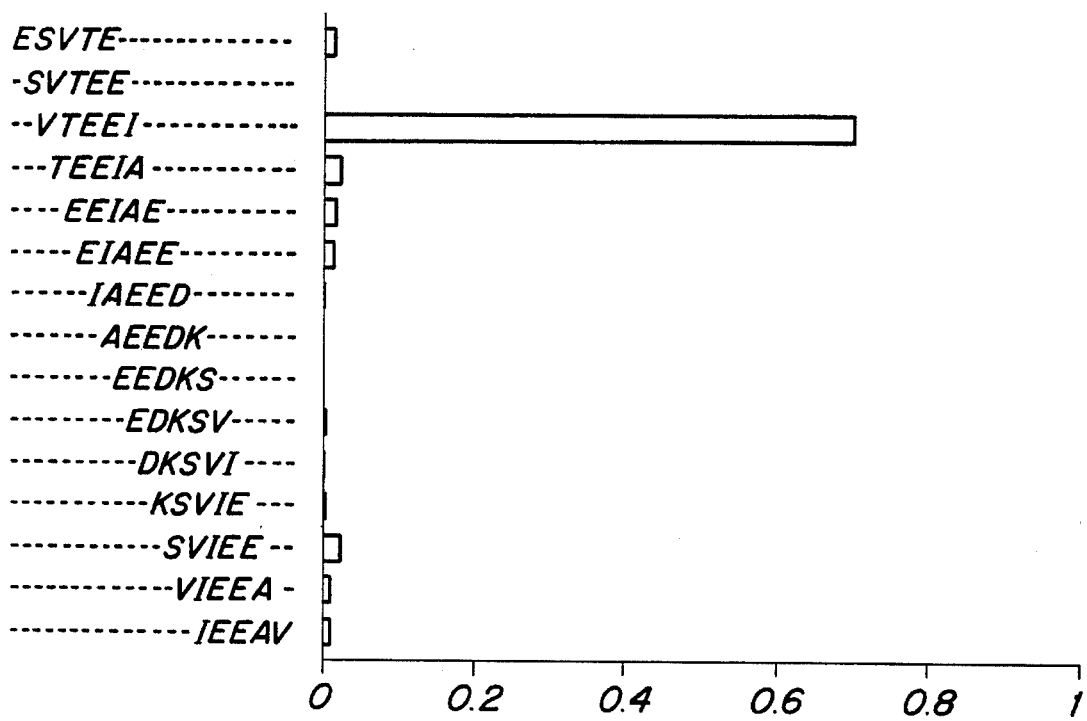
FIG. 1c shows antibody reactivity of one pentapeptide [SEQ ID NO. 12] according to the invention expressed as absorbance at 405 nm.
Figure 1D:
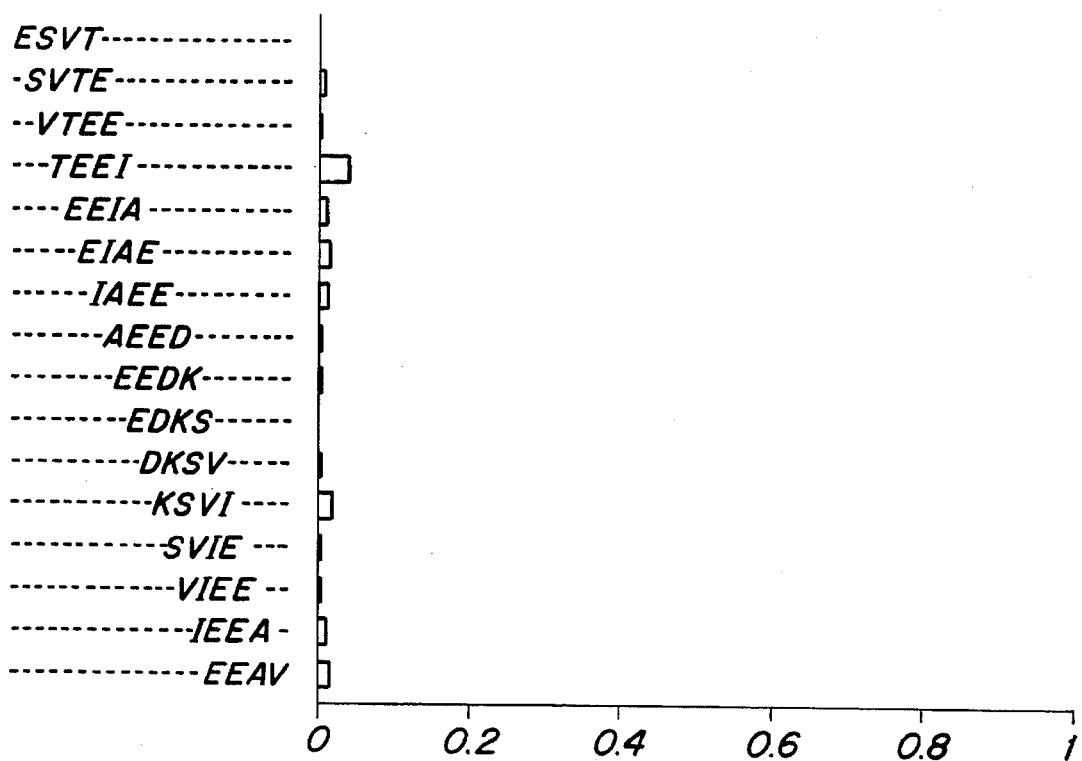
FIG. 1d shows antibody reactivity against any of the 16 tetrapeptides according to the invention expressed as absorbance at 405 nm.
Figure 2:
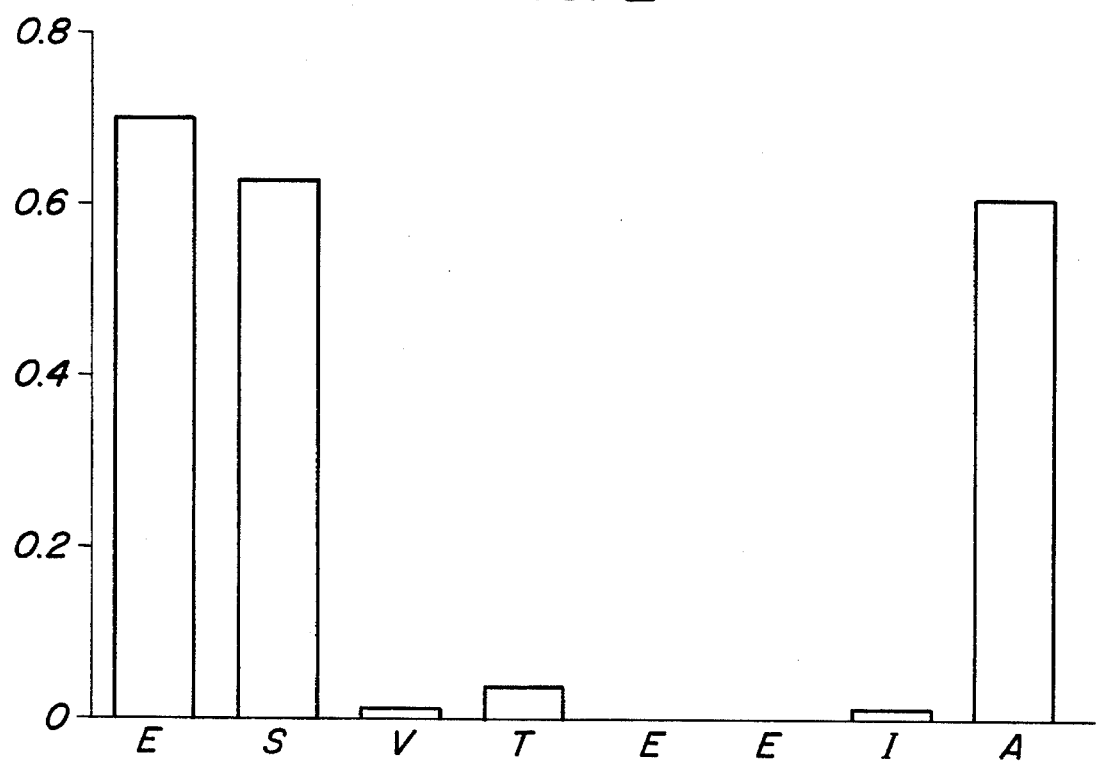
FIG. 2 shows antibody reactivity to peptides according to the invention also expressed as the absorbance at 405 nm.

The antibody showed reactivity with four heptapeptides corresponding to amino acids 1–7[SEQ ID NO.: 3] (ESVTEEI), 2–8 [SEQ ID NO.: 4] (SVTEEIA), 3–9 [SEQ ID NO.: 5] (VTEEIAE) and 4–10 [SEQ ID NO.: 13] (TEEIAEE) (FIG. 1a). When tested against hexapeptides the antibody recognized sequences corresponding to amino acids 2–7 [SEQ ID NO.: 6] (SVTEEI), 3–8 [SEQ ID NO.: 7] (VTEEIA) and 4–9 [SEQ ID NO. 14] (TEEIAE) (FIG. 1b). Reactivity to pentapeptides was restricted to one peptide, corresponding to amino acids 3–7 [SEQ ID NO: 8] (VTEEI) (FIG. 1c), while no reactivity was seen with any of the tetrapeptides (FIG. 1d). When tested against eight heptapeptides corresponding to the sequence ESVTEEIA (amino acids 1–8 [SEQ ID NO.:16]), where one amino acid residue had been omitted in each peptide, the antibody could not recognize peptides where either V, T, E, E or I had been excluded (FIG. 2).

Figure 3:
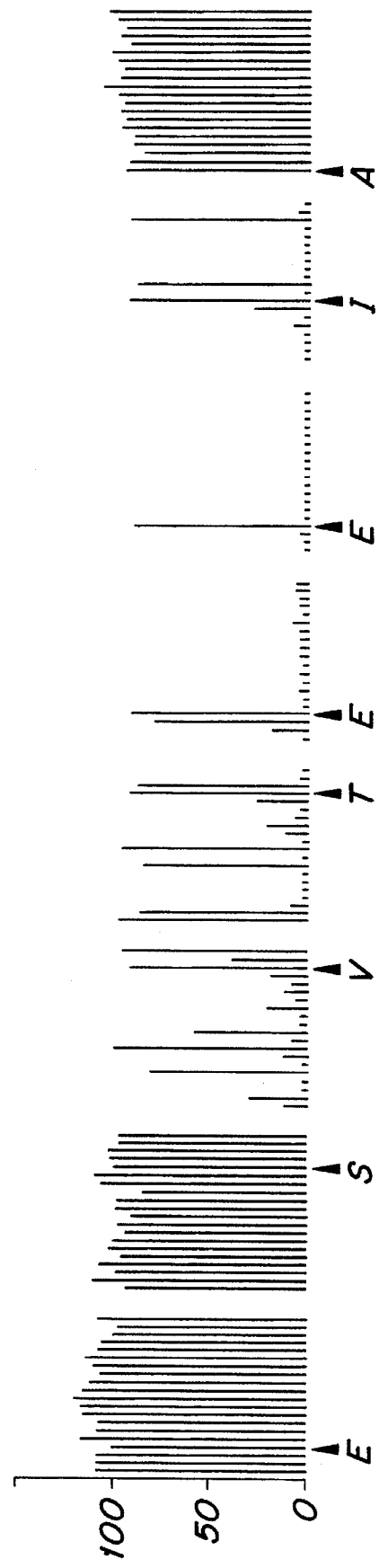
FIG. 3 shows a replacement set analysis of 33G2 reactivity to an octapeptide.

The mAb 33G2 was analyzed for reactivity against octapeptides [SEQ ID NO.:16] based on the sequence ESVTEEIA, where single amino acid substitutions replaced each residue. Every residue in the parent peptide [SEQ ID NO.:16] ESVTEEIA, which corresponds to residue 1–8 of the known sequence of Ag332, was replaced by the most common 20 amino acids (FIG. 3). The first (E), second (S) and last amino acid residue (A) were shown to be replaceable by any other amino acid without loosing the ability of the monoclonal 33G2 to recognize the peptides. A linear, five amino acid, sequence [SEQ ID NO.:8] (VTEEI) was shown to consist of amino acids which were either essential or replaceable mainly by amino acids of resembling chemical character. Substitution of valine (V) by C, F, I, L, P, T, W and Y, and threonine (T) by A, C, I, L, P, S, and V, gave ELISA absorbance values of 20% or more compared to the values obtained with the parent octapeptides. The pair of glutamic acids (E), contained within the epitope, were the most essential residues. The first glutamic acid (E) was totally nonreplaceable while the second glutamic acid (E) was possible to replace with aspartic acid (D), a very conserved replacement, and to some extent with cysteine (C). The last amino acid within the epitope, isoleucine (I), was possible to replace with leucine (L) and valine (V), two relatively conserved replacements. It could also be replaced to some degree by the positively charged amino acid histidine (H).

Figure 4:
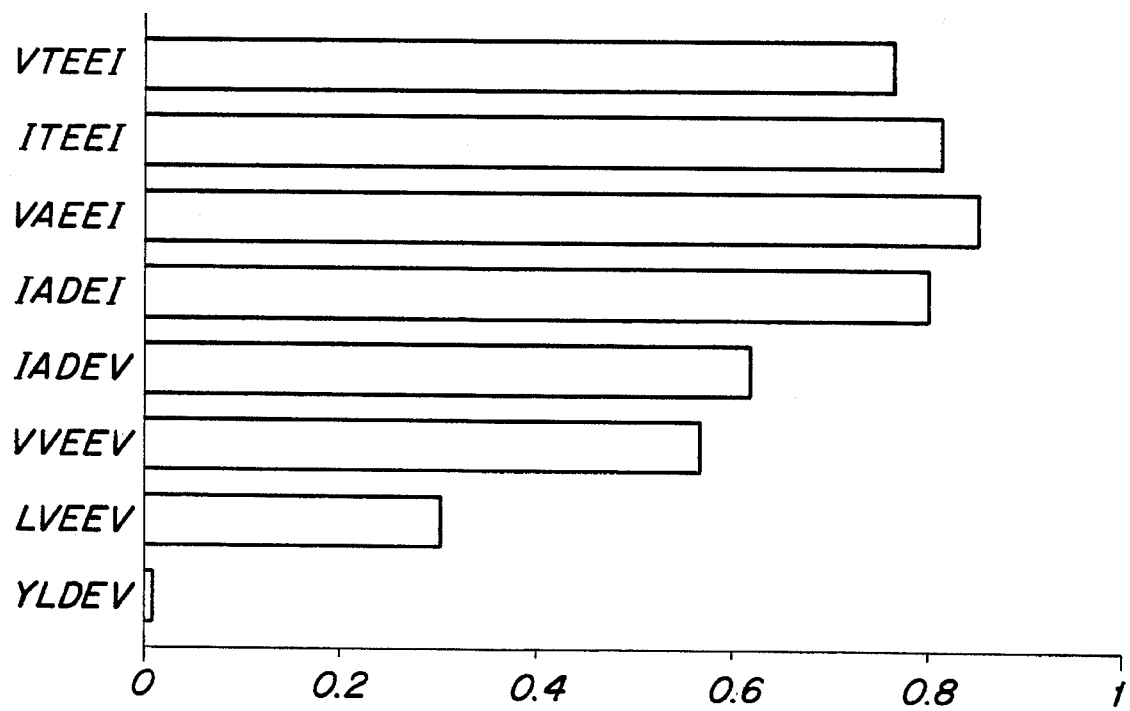
FIG. 4 [SEQ ID NOS.: 9–12, 17–20] shows antibody reactivity to epitope analogs expressed as the absorbance at 405 nm.

Based on the results in the replacement set analysis, pentapeptides corresponding to residue 3–7 of Ag332 were constructed in which one or several original amino acids had been replaced simultaneously. The results from this assay showed that it was possible to replace several amino acids within the epitope, simultaneously, without loosing antibody reactivity (FIG. 4). The antibody recognized most of the peptides where the modifications were consistent with the results from the replacement set analysis; ITEEI [SEQ ID NO.:9], VAEEI [SEQ ID NO.:10], IADEI [SEQ ID NO.:11], IADEV [SEQ ID NO.:17], VVEEV [SEQ ID NO.:19] and LVEEV [SEQ ID NO.:19]. A decrease in antibody reactivity could be seen for some peptides where several amino acids were replaced. The antibody did not react with the pentapeptide, YLDEV [SEQ ID NO.:20], indicating that not all of the reactive single amino acid substitutions can be performed simultaneously and still result in reactive peptides.

We claim:

1. A peptide consisting of an amino acid sequence selected from:
- glu-ser-val-thr-glu-glu-ile (SEQ ID NO. 3);
- ser-val-thr-glu-glu-ile-ala (SEQ ID NO. 4);
- val-thr-glu-glu-ile-ala-glu (SEQ ID NO. 5);
- ser-val-thr-glu-glu-ile (SEQ ID NO. 6);
- val-thr-glu-glu-ile-ala (SEQ ID NO. 7);
- val-thr-glu-glu-ile (SEQ ID NO. 8);
- ile-thr-glu-glu-ile (SEQ ID NO. 9);
- val-ala-glu-glu-ile (SEQ ID NO. 10); and
- ile-ala-asp-glu-ile (SEQ ID NO. 11).

2. A peptide according to claim 1, wherein said amino acid sequence is:
- val-thr-glu-glu-ile (SEQ ID NO. 8).

3. A peptide consisting of an amino acid sequence selected from:
- thr-glu-glu-ile-ala-glu-glu (SEQ ID NO. 13); and
- thr-glu-glu-ile-ala-glu (SEQ ID NO. 14).

4. A pharmaceutical composition comprising a peptide according to claim 1 in admixture with a pharmaceutically acceptable carrier.

5. A pharmaceutical composition according to claim 4, wherein said carrier is suitable for parenteral administration.

6. A pharmaceutical composition according to claim 4 wherein said peptide is present in polymerized form.

7. A pharmaceutical composition according to claim 4 wherein said peptide is coupled to a carrier molecule.

8. A pharmaceutical composition according to claim 4 wherein said peptide is coupled to an immunogenic carrier.

9. A pharmaceutical composition comprising a peptide according to claim 2 in admixture with a pharmaceutically acceptable carrier.

10. A pharmaceutical composition comprising a peptide according to claim 3 in admixture with a pharmaceutically acceptable carrier.

11. A pharmaceutical composition according to claim 5 wherein said peptide is present in polymerized form.

12. A pharmaceutical composition according to claim 5 wherein said peptide is coupled to a carrier molecule.

13. A pharmaceutical composition according to claim 5 wherein said peptide is coupled to an immunogenic carrier.

14. A method of inducing immunity against malaria induced by *Plasmodium falciparum* which comprises administering to a person in need of such immunity an effective amount of the pharmaceutical composition of claim 4.

15. A method according to claim 14, wherein the administration is constituted by parenteral injection.

16. A method of immunizing a mammal, said method comprising administering an effective amount a peptide according to claim 1.

17. The method of claim 16, wherein said mammal is immunized against malaria.

18. A method of immunizing a mammal, said method comprising administering an effective amount of a peptide according to claim 2.

19. The method of claim 18, wherein said mammal is immunized against malaria.

20. A method of immunizing a mammal, said method comprising administering an effective amount of a peptide according to claim 3.

21. The method of claim 20, wherein said mammal is immunized against malaria.

* * * * *